United States Patent [19]

van Zorge

[11] 4,327,213
[45] Apr. 27, 1982

[54] ALPHA-HYDROCARBONOXYIMINO-PYRAZINEACETONITRILES

[75] Inventor: Jacob A. van Zorge, Ameide, Netherlands

[73] Assignee: ACF Chemiefarma VA, Netherlands

[21] Appl. No.: 865,484

[22] Filed: Dec. 29, 1977

[30] Foreign Application Priority Data

Jan. 7, 1977 [GB] United Kingdom ............... 0624/77

[51] Int. Cl.³ ............................................ C07D 241/12
[52] U.S. Cl. ................................... 544/336; 424/250
[58] Field of Search ...................... 260/294.9; 544/336

[56] References Cited

U.S. PATENT DOCUMENTS 3,845,064  10/1974  Curran .................. 260/294.8 E
4,009,274  2/1977  Curran ..................... 260/294.9

FOREIGN PATENT DOCUMENTS 7609792  9/1976  Netherlands .
993746  6/1965  United Kingdom . .

OTHER PUBLICATIONS

Tyson et al. J. Org. Chem. vol. 34, pp. 3635–3638, (1969).
Burger Medicinal Chemistry 2nd Edition, p. 78, Interscience Publishers Inc. (1960).
Poziomer et al. J. Org. Chemistry, vol. 26, 3769–3771, (1961).

Primary Examiner—Jose Tovar
Attorney, Agent, or Firm—Jacobs & Jacobs

[57] ABSTRACT

Pharmaceutical compositions having anti-ulcer activity, containing as an active ingredient a compound of the formula

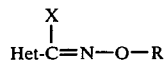

or a pharmaceutically acceptable salt thereof, wherein
Het is a heteroaromatic group (substituted or unsubstituted), containing one or more nitrogen atoms as hetero atoms and no more than two rings;
X is a hydrogen atom or a cyano, trifluoromethyl or an amido group with the formula—$C(A)NR^1R^2$, wherein A is oxygen or sulphur, $R^1$ is hydrogen or a $C_{1-4}$ alkyl group, $R^2$ is hydrogen or a $C_{1-4}$ alkyl group, or $R^1$ and $R^2$ together with the nitrogen atom to which they are attached form a 5- to 6-membered heterocyclic ring in which another hetero atom may be present; and
R is $C_{1-6}$ alkyl, $C_{5-6}$ cycloalkyl, $C_{5-8}$ cycloalkylalkyl, $C_{3-6}$ alkenyl, $C_{3-4}$ alkynyl, phenyl $C_{1-3}$ alkyl, the phenyl group being optionally substituted by one or more $C_{1-6}$ alkyl, halogen, $C_{1-6}$ alkoxy, nitro, cyano or trifluoromethyl groups, a carbamidoalkyl group with the formula—$(CH_2)_mC(O)NR^3R^4$ wherein m=1 or 2, $R^3$ is hydrogen or $C_{1-3}$ alkyl, $R^4$ is hydrogen or $C_{1-3}$ alkyl, or $R^3$ and $R^4$ together with the nitrogen atom to which they are attached form a 5- to 6-membered heterocyclic ring in which another hetero atom may be present, or cyano $C_{1-3}$ alkyl;

or an N-oxide or pharmaceutically acceptable salt thereof; novel compounds of the said formula and methods for preparing these compounds.

8 Claims, No Drawings

ALPHA-HYDROCARBONOXYIMINO-PYRAZINEACETONITRILES

The present invention relates to novel pharmaceutical compositions having anti-gastric ulcer activity, to certain oxime ether derivatives for use in these compositions, and to methods for the preparation of these compounds.

In J. Org. Chem. 34, 3635 (1969), the preparation of α-methoxyimino and α-benzyloxyimino-4-pyridineacetonitrile (O-methyl and O-benzyl 4-pyridineglyoxylonitrile) and α-methoxyimino-4-pyridineacetamide has been described, but no pharmacological activity was mentioned.

In Dutch patent application No. 76.09792 the oxime ether α-cyanomethoxyimino-phenylacetonitrile has been described as an antagonist of herbicide activity.

We have now found that certain oxime ethers derived from heterocyclic ketones possess anti-ulcer activity in the gastro-intestinal tract, e.g. by inhibition of gastric acid secretion and/or stimulation of mucus formation, and that these compounds and pharmaceutical compositions containing them may be used in the treatment of diseases of the gastro-intestinal tract.

Accordingly, the invention provides a pharmaceutical composition, which composition comprises a compound of the formula (I):

or a pharmaceutically acceptable salt thereof, wherein
Het is a heteroaromatic group (substituted or unsubstituted), containing one or more nitrogen atoms as hetero atoms and no more than two rings;
X is a hydrogen atom or a cyano, trifluoromethyl or an amido group with the formula $-C(A)NR^1R^2$, wherein A is oxygen or sulphur, $R^1$ is hydrogen or a $C_{1-4}$ alkyl group, $R^2$ is hydrogen or a $C_{1-4}$ alkyl group, or $R^1$ and $R^2$ together with the nitrogen atom to which they are attached form a 5- to 6-membered heterocyclic ring in which another hetero atom may be present; and
R is $C_{1-6}$ alkyl, $C_{5-6}$ cycloalkyl, $C_{5-8}$ cycloalkylalkyl, $C_{3-6}$ alkenyl, $C_{3-4}$ alkynyl, phenyl $C_{1-3}$ alkyl, the phenyl group being optionally substituted by one or more $C_{1-6}$ alkyl, halogen, $C_{1-6}$ alkoxy, nitro, cyano or trifluoromethyl groups, a carbamidoalkyl group with the formula $-(CH_2)_mC(O)NR^3R^4$ wherein m=1 or 2, $R_3$ is hydrogen or $C_{1-3}$ alkyl, $R^4$ is hydrogen or $C_{1-3}$ alkyl, or $R^3$ and $R^4$ together with the nitrogen atom to which they are attached form a 5- or 6-membered heterocyclic ring in which another hetero atom may be present, or cyano $C_{1-3}$ alkyl;
or an N-oxide or pharmaceutically acceptable salt thereof, together with a pharmaceutically acceptable carrier or diluent therefor.

One class of the compounds of formula (I) is that in which X and R are as defined above and Het is a pyrazinyl, pyrimidinyl, pyridinyl, imidazo-pyridinyl, quinoxalinyl, quinazolinyl, quinolinyl or iso-quinolinyl group, which groups may be optionally substituted by one or more $C_{1-6}$ alkyl, halogen or $C_{1-6}$ alkoxy groups; and N-oxides and/or pharmaceutically acceptable salts thereof.

Another sub-class of the compounds of formula (I) is that in which X and R are as defined above and Het is a pyrazinyl, pyrimidinyl, imidazopyridinyl, quinoxalinyl, quinazolinyl, quinolinyl or iso-quinolinyl group, which groups may be optionally substituted by one or more $C_{1-6}$ alkyl, halogen or $C_{1-6}$ alkoxy groups; and N-oxides and/or pharmaceutically acceptable salts thereof.

A further sub-class of the compounds of formula (I) is that in which Het is a pyrazinyl, pyrimidinyl, pyridinyl, imidazo-pyridinyl, quinoxalinyl, quinazolinyl or quinolinyl group, optionally substituted by one or more $C_{1-6}$ alkyl, halogen or $C_{1-6}$ alkoxy groups; X is a hydrogen atom or a cyano, trifluoromethyl or a group of the formula $-C(A)NR^1R^2$ wherein A is oxygen or sulphur, $R^1$ is hydrogen or a $C_{1-4}$ alkyl group, $R^2$ is hydrogen or a $C_{1-4}$ alkyl group, or $R^1$ and $R^2$ together with the nitrogen atom to which they are attached form a 5- to 6-membered heterocyclic ring; and R is a $C_{1-6}$ alkyl, $C_{5-6}$ cycloalkyl, $C_{5-8}$ cycloalkylalkyl or a phenyl $C_{1-3}$ alkyl group; and pharmaceutically acceptable salts thereof.

Examples of Het groups are pyrazinyl, 2-, 4- or 5-pyrimidinyl, 2-, 3- or 4-pyridinyl, 2- or 3-imidazo[1,2-a]pyridinyl, 2-quinoxalinyl, 2-, 3- or 4-quinolinyl optionally substituted by 6- or 7-methyl, chloro or methoxy, and 1-, 3- or 4-isoquinolinyl. Preferably, Het is pyrazinyl, 2- or 4-pyridinyl or 3-imidazo[1,2-a]pyridinyl, of which pyrazinyl and 2-pyridinyl are especially preferred and pyrazinyl is the most preferred.

Preferably, X is cyano, trifluoromethyl, thiocarbamoyl ($-C(S)NH_2$), N,N-diethylaminothiocarbonyl or morpholinothiocarbonyl, of which cyano is the most preferred.

Examples of R groups are methyl, ethyl, n- or iso-propyl, n- or tert-butyl, cyclopentyl, cyclohexyl, cyclohexylmethyl, allyl, propargyl, benzyl, optionally substituted by p-methyl, p-chloro, p-methoxy, p-nitro, p-trifluoromethyl, p-cyano, phenethyl, carbamoylmethyl ($CH_2C(O)NH_2$), dimethylaminocarbonylmethyl, cyanomethyl, and the like. Preferably R is methyl, ethyl, allyl, propargyl, benzyl, phenethyl or cyanomethyl, the methyl group being the most preferred.

Examples of N-oxides are the N-oxides of a compound of formula (I), in which Het is pyrazinyl or 2-pyridinyl.

The pharmaceutically acceptable salts include the therapeutically appropriate acid salts and quaternary addition salts. Among the pharmaceutically acceptable acids, which are suitable for the formation of addition salts, are inorganic acids, such as hydrochloric acid, hydrobromic acid, sulphuric acid, nitric acid, phosphoric acid, and organic acids, such as citric acid, acetic acid, oxalic acid, fumaric acid, lactic acid, succinic acid, tartaric acid and methanesulphonic acid, of which hydrochloric acid, sulphuric acid and methanesulphonic acid are preferred.

An example of quaternary addition salts is the methiodide salt of the compounds of formula I.

From the aforesaid it will be seen that one particularly useful class of compounds within formula (I) is of formula (I)':

wherein

Het' is pyrazinyl, 2- or 4-pyridinyl or 3-imidazo[1,2-a]pyridinyl;

X' is cyano, thiocarbamoyl or morpholinothiocarbonyl; and

R' is methyl, ethyl, allyl, propargyl, cyanomethyl, benzyl or phenethyl; and addition salts thereof.

Preferably Het' is pyrazinyl, X' is cyano and R' is methyl, ethyl, allyl, propargyl or benzyl, most preferably methyl.

Especially preferred compounds of formula (I)' are α-methoxyiminopyrazineacetonitrile (most preferred),
α-methoxyimino-2-pyridineacetonitrile,
α-methoxyimino-4-pyridineacetonitrile,
α-methoxyimino-3-imidazo[1,2-a]pyridineacetonitrile,
α-methoxyimino-4-quinolineacetonitrile,
α-ethoxyiminopyrazineacetonitrile,
α-allyloxyiminopyrazineacetonitrile,
α-propargyloxyiminopyrazineacetonitrile,
α-benzyloxyiminopyrazineacetonitrile, and
α-cyanomethyloxyiminopyrazineacetonitrile.

The pharmacological properties and the pharmacological activity of the compounds of the formula (I) (and their N-oxides and salts) vary with the nature of the groups Het, X and R. Thus, some compounds will have a greater pharmacological activity than others. Some compounds have a relatively low pharmacological activity (e.g. when X is a carboxamido group), but they are particularly useful as intermediates in the preparation of other, more active compounds of formula (I).

It will be realized that the compounds with formula (I) may exist in two different forms (E and Z isomers). All such forms are included within this invention.

The compounds of formula (I) (apart from α-methoxyimino-4-pyridineacetonitrile, α-benzyloxyimino-4-pyridineacetonitrile, and α-methoxyimino-4-pyridineacetamide) and their N-oxides and pharmaceutically acceptable salts are novel and constitute a further aspect of the present invention.

The compounds of formula (I) (by which, hereinafter, we include the N-oxides and pharmaceutically acceptable salts) can be prepared according to methods which are known per se for the preparation of this type of compound, or methods analogous thereto.

A suitable method for the preparation of a compound of formula (I) comprises the reaction of a compound of formula (II):

(II)

wherein Het and X are as defined in relation to formula (I) and M is a hydrogen or an alkali metal atom, with a compound of formula (III):

R—Y (III)

wherein R is as defined in relation to formula (I) and Y is a suitable leaving group, such as a chloride, bromide, iodide or a tosyloxy group.

The reaction may be carried out in a solvent, such as methanol, ethanol, acetone, methyl ethyl ketone, dioxane, dimethylglycol ether or dimethyl formamide. If, in formula (II), M represents a hydrogen atom, it may be useful to add an acid binding agent to the reaction mixture. Suitable acid binding agents are, for example, alkali metal hydrides, hydroxides, carbonates and alkoxides, tertiary amines, pyridine and the like. The reaction conditions are as commonly used for this type of reaction. Usually, the reaction temperature will be between room temperature and the boiling temperature of the reaction mixture.

The conversion of the oxime compound (II) into compound (I) is usually effected by alkylation with an alkyl, cycloalkyl, cycloalkylalkyl, alkenyl, alkynyl, phenylalkyl, carbamidoalkyl, carboxyalkyl or cyanoalkyl halide, such as the chloride, bromide or iodide, in the presence of, for instance, sodium hydride, or an alkali metal hydroxide or alkoxide, preferably sodium methoxide, dissolved in a suitable solvent, preferably dimethyl formamide or methyl alcohol.

The conversion of compounds (I) and (II), when X is a cyano group, into the corresponding carboxamide or thioamido group may take place by conventional methods, of course, in so far as they do not affect other groups. Suitably, the cyano group can be converted to a thioamido group by treating the compound with hydrogen sulphide, followed, if desired, by alkylation, for example with a dialkyl sulphate. Another method comprises the conversion of the cyano compound to the corresponding carboxamide in a conventional manner, followed, if desired, by treating the obtained compound with phosphorus pentasulphide.

The conversion of the obtained compound of formula (I), when R is carboxyalkyl, into the compound in which R is carbamidoalkyl may take place by conventional methods.

Another suitable method for the preparation of a compound of formula (I) comprises the reaction of a compound of formula (IV):

(IV)

wherein Het and X are as defined in relation to formula (I) and C=Q is a carbonyl group or a protected carbonyl group, with a O-substituted hydroxylamine derivative of formula (V):

H$_2$N—O—R (V)

or a salt thereof, wherein R is as defined in relation to formula (I).

Suitable protected carbonyl groups are, for example, ketals and oximes. The preferred meaning of Q is oxygen. If Q is an alkylenedioxy group, the preferred meaning is ethylenedioxy.

The reaction may be carried out under reaction conditions which are commonly used for this type of reaction. Preferably, the reaction is carried out in a solvent, such as an alcohol, dioxane, dimethyl formamide, tetrahydrofuran or pyridine.

The compound (V) is preferably added in the form of its acid salt, preferably its hydrochloride, to compound (IV) which is preferably dissolved in pyridine.

Generally, the preferred method of preparing a compound of formula (I) depends on the choice of the compound to be prepared.

It will be clear to those skilled in the art that in a number of cases certain reaction steps described may be carried out in a different sequence or simultaneously or without isolating intermediates, and these possibilities are all included in the invention. For example, the introduction of the group R in compound (I) according to the reaction of compound (IV) with compound (V) may also be carried out by reacting compound (IV) with a compound of formula (VI):

H₂N—O—Z  (VI)

wherein Z is a group replaceable by or convertable into R, R being as hereinbefore defined. The obtained compound of formula (VII):

$$\underset{Het\text{-}C=N-O-Z}{\overset{X}{|}} \quad (VII)$$

wherein Het, X and Z are as hereinbefore defined, can then be converted to the compound of formula (I).

The N-oxides (of the compounds of formula (I)) are preferably prepared by reacting a compound of formula (I) with a peroxide, for example, hydrogen peroxide, benzoyl peroxide, or a similar compound, of which hydrogen peroxide is preferred. The reaction is preferably carried out in an inert solvent, such as, for example, acetic acid, propionic acid, or the like, at temperatures generally ranging between 50° C. and 90° C.

The N-oxides can also be prepared by reacting a compound of formula (IV), wherein Het is the N-oxide of the previously defined hetero group (instead of the hetero group itself), with a hydroxylamine derivative of formula (V), in the manner hereinbefore described.

The pharmaceutically acceptable salts can be prepared in conventional manner.

The separation of the E and Z isomers may be effected by conventional methods, preferably by column chromatography.

The preparation of the intermediate oxime compounds of formula (II) and their salts may occur by methods which are known for the preparation of this type of compound and methods analogous thereto. Some of the oxime compounds of formula (II) are known. For example, in J. Org. Chem. 26, 3769 (1961) the preparation of the oximes of formula (II) have been described, in which Het is 2-pyridinyl, 2-(3-methyl-pyridinyl), 4-pyridinyl, 4-quinolinyl, and X is cyano.

A preferred method for the preparation of a compound of formula (II) comprises the reaction of a compound of formula (VIII):

Het—CH₂—X¹  (VIII)

wherein Het is as defined in relation to formula (I) and X¹ is a cyano, trifluoromethyl, or amido or thioamido group with the formula —C(A)NR¹R², wherein A is oxygen or sulphur, R¹ and R² are the same or different C₁₋₄ alkyl groups or, together with the nitrogen atom to which they are attached, form a 5- or 6-membered heterocyclic ring in which another hetero atom may be present, with a suitable nitrite compound.

Suitable nitrite compounds include nitrous acid-generating salts or esters. If the methylene group from the starting compound (VIII) is relatively active, e.g. when Het is pyrazinyl and X¹ is a cyano group, the conventional and preferred solvent being glacial acetic acid.

When the methylene group from the starting compound (VIII) is relatively less active, e.g. if the —CH₂X¹ group is not in an α- or γ-position with respect to at least one nitrogen atom of the heterocyclic group Het, e.g. if Het is a 3-pyridyl group, suitable nitrite compounds for the conversion of compound (VIII) into compound (II) include alkyl nitrites, preferably n-butyl nitrite, in a suitable solvent, preferably methyl alcohol, in the presence of an alkali metal alkoxide, preferably sodium methoxide. After acidifying, e.g. with acetic acid, compound (II) may be isolated.

Another method for the preparation of the oximes of formula (II) comprises the reaction of a compound of formula (IX):

$$\underset{Het\text{-}C=Q^1}{\overset{X}{|}} \quad (XI)$$

wherein Het and X are as hereinbefore described and Q¹ is oxygen or alkylenedioxy, preferably ethylenedioxy, with hydroxylamine. The reaction conditions and, if desired, the solvent are as commonly used for this type of reaction.

In a number of cases, certain reaction steps described may be carried out in a different sequence or simultaneously or without isolating intermediates, and these possibilities are all included in the invention. If, for example, the introduction of the oxime group in a compound of formula (VIII) is carried out with an alkyl nitrite, the following alkylation step can also be performed without isolating the oxime compound (II), by omitting the acidifying step and adding the alkyl, cycloalkyl, etc. halide to the reaction medium, the medium being made weakly alkaline for the latter reaction.

The compositions may be in the form of tablets, capsules, powders, granules, lozenges or liquid preparations, such as oral or sterile parenteral solutions or suspensions.

Clearly the formulation of the said pharmaceutical composition will depend on the nature of the activity shown by the chosen compound of the formula (I), and on other factors such as a preference in a particular area of therapy for a particular mode of administration.

Tablets and capsules for oral adminstration may be in unit dose presentation form, and may contain conventional excipients such as binding agents, fillers, tabletting lubricants, disintegrants, and acceptable wetting agents and the like. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, emulsifying agents, non-aqueous vehicles (which may include edible oils), preservatives, and if desired conventional flavouring or colouring agents, and the like.

For the parenteral administration, fluid unit dosage forms are prepared utilizing the compound of the formula (I) and a sterile vehicle. The compound, depending on the vehicle and concentration used, can be either suspended or dissolved in the vehicle. In preparing solutions the compound can be dissolved for injection and filter sterilized before filling into a suitable vial or ampoule and sealing. Advantageously, adjuvants such as a local anaesthetic, preservatives and buffering agents can be dissolved in the vehicle. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

When appropriate the compositions of this invention may be presented as an aerosol for oral administration, or as a microfine powder for insufflation.

As is common practice, the compositions will usually be accompanied by written or printed directions for use in the medical treatment concerned.

It will of course be realized that the precise dosage used in the treatment of any of the hereinbefore described disorders will depend on the actual compound of the formula (I) used, and also on other factors such as the seriousness of the disorder being treated. Broadly, the dose may vary from about 100 mg up to about 25 g per day per patient.

The invention also provides a method of treatment and/or prophylaxis of gastric disorders in human beings which comprises the administration to the sufferer of an effective amount of a compound of the formula (I). The "effective amount" of a compound of formula (I) will of course vary with factors such as the severity of the ulceration, the weight of the sufferer and the specific compound of the formula (I) used.

The following Examples illustrate the preparation of compounds of the formula (I) and their pharmacological properties.

EXAMPLE 1

α-Hydroxyiminopyrazineacetonitrile (intermediate compound)

Pyrazineacetonitrile (32 g), prepared as described in British Patent Specification No. 1 021 397, was dissolved in glacial acetic acid (250 ml). The solution was stirred and 1.2 equivalents of sodium nitrite (22.3 g) were added in small portions, while the temperature was kept under 20° C. After the addition, the reaction mixture was stirred at room temperature for another two hours. The title compound separated partly from the reaction mixture. On evaporation of the solvent under reduced pressure, a solid was obtained which on recrystallization from hot water yielded α-hydroxyiminopyrazineacetonitrile (35 g, 88%). Melting point >192° C. (dec.).

EXAMPLE 2 a. α-Hydroxyimino-2-pyridineacetonitrile (intermediate compound)

In a manner identical to that described in Example 1, but starting from 2-pyridineacetonitrile, the title compound was obtained in a yield of 80%. Melting point 209° C. (dec.) after crystallization from methanol/water.

In the same way the following α-hydroxyiminoacetonitrile derivatives were obtained:

$$\text{Het-}\underset{\underset{\text{CN}}{|}}{C}=N-O-H$$

| Het | m.p. (°C.) |
|---|---|
| b. 4-pyridinyl | 273–275 dec. |
| c. 2-quinolinyl | + |
| d. 4-quinolinyl | + |
| e. 1-isoquinolinyl | + |
| f. 3-isoquinolinyl | + |
| g. 2-quinoxalinyl | + |
| h. 6-chloro-2-quinolinyl | + |
| i. 7-chloro-2-quinolinyl | + |

-continued $$\text{Het-}\underset{\underset{\text{CN}}{|}}{C}=N-O-H$$

| Het | m.p. (°C.) |
|---|---|
| j. 6-methoxy-2-quinolinyl | + |
| k. 7-methoxy-2-quinolinyl | + |
| l. 6-methyl-2-quinolinyl | + |
| m. 7-methyl-2-quinolinyl | + |
| n. 4-methoxy-2-pyridinyl | + |
| o. 5-ethyl-2-pyridinyl | + |
| p. 6-chloro-2-pyridinyl | + |

+ Not purified. Crude product was directly used in the next reactions.

EXAMPLE 3 a. α-Hydroxyimino-3-pyridineacetonitrile (intermediate compound)

To a stirred solution of sodium ethoxide in anhydrous ethanol, prepared from 5 g of sodium and 50 ml of anhydrous ethanol, 24 g of 3-pyridineacetonitrile was added, followed by dropwise addition of 21 g freshly distilled n-butyl nitrite. The reaction mixture was stirred for another hour and the precipitated sodium salt of the oxime was filtered and washed with ether. The free oxime was obtained by acidification of an aqueous solution of the salt and recrystallization from water, yielding 17 g (58%) of the title compound. M.p. 234°–238° C. under decomposition. Usually, the salt was directly used in succeeding reactions.

In the same way the following α-hydroxyiminoacetonitrile derivatives were obtained:

$$\text{Het-}\underset{\underset{\text{CN}}{|}}{C}=N-O-H$$

| Het | m.p. (°C.) |
|---|---|
| b. 5-pyrimidinyl | + |
| c. 2-imidazo[1,2-a]pyridinyl | 234–235 dec. |
| d. 3-imidazo[1,2-a]pyridinyl | >225 dec. |

+ Not purified. Crude product was directly used in the next reactions.

EXAMPLE 4 a. α-Hydroxyimino-N,N-dimethyl-2-pyridinethioacetamide (intermediate compound)

In a manner similar to that described in Example 1, but starting from N,N-dimethyl-2-pyridinethioacetamide instead of pyrazineacetonitrile, the title compound was obtained, m.p. 120°–121° C.

The starting compound can be obtained in several ways, see for instance German Offenlegungsschrift No. 20 32 738, Organic Reactions III chapter 2 and R. Wegler et al in "Neuere Methoden der Präparativen Organischen Chemie", Band III chapter 1 (p. 31).

In the same manner the following compounds were obtained:

b. α-hydroxyimino-N,N-diethyl-2-pyridinethioacetamido+ c. α-hydroxyimino-4-(2-pyridinylthioacetyl)morpholine (m.p. 213°–214° C. dec.).

d. α-hydroxyimino-4-(pyrazinylthioacetyl)morpholine+

+Not purified. Crude product was directly used in the next reaction.

EXAMPLE 5

α-Methoxyiminopyrazineacetonitrile

α-Hydroxyiminopyrazineacetonitrile (35 g), prepared as described in Example 1, was added to 1.1 equivalents of sodium methoxide in methanol (300 ml) and the mixture was refluxed for two hours. The sodium salt of the oxime separated as a cream coloured solid. Methyl iodide (1.5 eq., 52 g) was added and the reaction mixture was refluxed until the solid disappeared and a dark brown solution was obtained. Methanol was evaporated under reduced pressure and the residue was shaken with water and ethyl acetate. The organic layer was separated and dried over magnesium sulphate. Evaporation of the solvent yielded a dark residue, which was disilled under reduced pressure and recrystallised from petroleum ether (b.p. 40°–60° C.), containing about 10% of ether, or purified by chromatography (SiO$_2$ column, cyclohexane-ethyl acetate 2:1) and then crystallized from petroleum ether (b.p. 40°–60° C.), containing about 10% of ether.

The α-methoxyiminopyrazineacetonitrile was obtained in a 75% yield (29 g), m.p. 63°–64° C.

From NMR-spectra this compound appeared to be the Z-isomer. The E-isomer was obtained by photochemical isomerization in benzene, followed by column chromatography of the obtained mixture (silica gel with cyclohexane-ethyl acetate 3:1 as the eluant). Melting point 64°–65° C. after recrystallization from petroleum ether (40°–60° C.).

EXAMPLE 6 a. α-Methoxyimino-2-pyridineacetonitrile

In a similar manner to that described in Example 5, but starting from α-hydroxyimino-2-pyridineacetonitrile, prepared as described in Example 2, the title compound was prepared in a yield of 90%. Melting point after crystallization from petroleum ether (b.p. 40°–60° C.) 68°–69° C. In the same manner the oxim ethers were obtained:

$$\text{Het-C}(\text{X})=\text{N}-\text{O}-\text{R}$$

| Het | X | R | Y (from RY) | isomer | m.p. °C. |
|---|---|---|---|---|---|
| b. pyrazinyl | cyano | ethyl | iodide | Z | 43–44 |
| c. pyrazinyl | cyano | iso-propyl | bromide | Z | 99–100 (methane sulphonate) |
| d. pyrazinyl | cyano | n-butyl | bromide | Z | oil |
| e. pyrazinyl | cyano | cyclohexyl | bromide | Z | 48–49 |
| f. pyrazinyl | cyano | cyclohexylmethyl | bromide | Z | 62–64 |
| g. pyrazinyl | cyano | allyl | bromide | Z | 152 dec. (hydrobromide) |
| h. pyrazinyl | cyano | propargyl | chloride | Z | 59–60 |
| i. pyrazinyl | cyano | cyanomethyl | chloride | Z | 106–107 |
| j. pyrazinyl | cyano | benzyl | chloride | Z | 111–113 |
| k. pyrazinyl | cyano | 4-methoxybenzyl | chloride | Z | 106–108 |
| l. pyrazinyl | cyano | 4-chlorobenzyl | chloride | Z | 83–84 |
| m. pyrazinyl | cyano | 4-nitrobenzyl | chloride | Z | 134–135 |
| n. pyrazinyl | cyano | 4-cyanobenzyl | bromide | Z | 133–134 |
| o. pyrazinyl | cyano | phenethyl | bromide | Z | 64–65 |
| p. pyrazinyl | cyano | carboxymethyl | chloride | Z | 194 dec. (this is an intermediate compound) |
| q. pyrazinyl | cyano | carbamoylmethyl | chloride | Z | 158–160 |
| r. pyrazinyl | cyano | N,N-dimethylaminocarbonylmethyl | chloride | Z | 168–170 |
| s. pyrazinyl | thiocarbonylmorpholide | methyl | iodide |  | 94–95 |
| t. 2-pyridinyl | cyano | n-butyl | bromide |  | oil |
| u. 2-pyridinyl | cyano | benzyl | chloride |  | 77–78 |
| v. 2-pyridinyl | N,N-dimethylaminothiocarbonyl | methyl | iodide |  | 121–124 |
| w. 2-pyridinyl | N,N-diethylaminothiocarbonyl | methyl | iodide |  | oil |
| x. 2-pyridinyl | thiocarbonylmorpholide | methyl | iodide |  | 142–144 |
| y. 4-methoxy-2-pyridinyl | cyano | methyl | iodide |  | 68–70 |
| z. 5-ethyl-2-pyridinyl | cyano | methyl | iodide |  | 60–61 |
| aa. 6-chloro-2-pyridinyl | cyano | methyl | iodide |  | 106–108 |
| bb. 3-pyridinyl | cyano | methyl | iodide |  | 143–144 (hydrochloride) |
| cc. 4-pyridinyl | cyano | methyl | iodide |  | 68–69 |
| dd. 5-pyrimidinyl | cyano | methyl | iodide |  | 120–125 (hydrochloride methanol) |
| ee. 2-quinolinyl | cyano | methyl | iodide | Z | 117–118 |
| ff. 6-methyl-2-quinolinyl | cyano | methyl | iodide | Z | 138–139 |
| gg. 7-methyl-2-quinolinyl | cyano | methyl | iodide | Z | 113–114 |
| hh. 6-methoxy-2-quinolinyl | cyano | methyl | iodide | Z | 174–175 |
| ii. 7-methoxy-2-quinolinyl | cyano | methyl | iodide | Z | 166–167 |
| jj. 6-chloro-2-quinolinyl | cyano | methyl | iodide | Z | 151–152 |
| kk. 7-chloro-2-quinolinyl | cyano | methyl | iodide | Z | 171–173 |
| ll. 4-quinolinyl | cyano | methyl | iodide | Z | 95–97 |
| mm. 1-isoquinolinyl | cyano | methyl | iodide | Z | 111–113 |
| nn. 2-quinoxalinyl | cyano | methyl | iodide | Z | 154–156 |
| oo. 2-imidazo[1,2-a]pyridinyl | cyano | methyl | iodide | E | 162–165 |
| pp. 2-imidazo[1,2-a]pyridinyl | cyano | methyl | iodide | Z | 168–170 |

-continued

| | | | Y | | |
|---|---|---|---|---|---|
| Het | X | R | (from RY) | isomer | m.p. °C. |
| qq. 3-imidazo[1,2-a]pyridinyl | cyano | methyl | iodide | E | 132–133 |
| rr. 3-imidazo[1,2-a]pyridinyl | cyano | methyl | iodide | Z | 162–164 |

$$\text{Het-C}(X)=N-O-R$$

EXAMPLE 7

2-Pyridinyl trifluoromethyl ketone, O-methyl oxime

A mixture of 8.5 g of 2-pyridinyl trifluoromethyl ketone (Tetrahedron 27, 1221 (1972)), 6 g O-methylhydroxylamine hydrochloride and 6 ml of pyridine was refluxed for 8 hours. The reaction mixture was concentrated under reduced pressure and the residue was stirred with water and ethyl acetate. The organic layer was separated and dried over magnesium sulphate.

Evaporation of the solvent and distillation under reduced pressure afforded the desired product as a colourless oil, b.p. 90°–91° C./14.

EXAMPLE 8

α-Methoxyimino-2-pyridinethioacetamide (Z-isomer)

A solution of 1.23 g of hydrogen sulphide and 5.86 g of α-methoxy-imino-2-pyridineacetonitrile in 50 ml of pyridine was stirred in a closed vessel for 17 hours. The reaction mixture was then concentrated under reduced pressure and the residue crystallized from a mixture of methanol and ether. Yield 0.6 g, m.p. 155°–156° C.

EXAMPLE 9 a. α-Methoxyiminopyrazineacetamide (Z-isomer)

α-Methoxyiminopyrazineacetonitrile Z-isomer (6.0 g) was dissolved in 35 ml of methanol. A solution of potassium hydroxide (4 g) in 10 ml of water was added and the dark reaction mixture was stirred for 1 hour at a temperature of 40° C. The greater part of the methanol was evaporated under reduced pressure.

Acidification and successive filtration of the precipitate afforded Z-α-methoxyiminopyrazineacetamide which was recrystallized from water. M.p. 188°–190° C., yield 3.1 g.

In the same way were obtained:

b. α-methoxyimino-2-pyridinylacetamide, Z-isomer, m.p. 147°–148° C.
c. α-methoxyimino-2-pyridinylacetamide, E-isomer, m.p. 123°–124° C.
d. α-methoxyimino-4-pyridinylacetamide, m.p. 147°–148° C.

EXAMPLE 10

α-Methoxyimino-2-pyridinethioacetamide (Z-isomer)

The same compound as described in Example 8 was obtained by treating the corresponding carboxamide (Example 9b) with P$_2$S$_5$ in pyridine (cf. German Offenlegungsschrift No. 20 32 738).

EXAMPLE 11

N-methyl-α-methoxyimino-2-pyridineacetamide (E and Z-isomer)

Z-α-methoxyimino-2-pyridineacetic acid methylester (5 g) and a solution of methylamine in water (15 ml, 30%) were stirred at a temperature of 60° C. until the starting compound was completely dissolved. Water was evaporated under reduced pressure and the residue was recrystallized from toluene, yielding N-methyl-α-methoxyimino-2-pyridineacetamide (3.0 g), Z-isomer, m.p. 132°–133° C. The E-isomer was obtained in the same way, but starting from the corresponding E-ester. M.p. of the E-isomer 91°–93° C.

The α-methoxyimino-2-pyridineacetic acid methylesters were prepared by dissolving 15 g of the corresponding α-hydroxyimino-2-pyridineacetic acid ethylesters in 150 ml of methanol, containing 5.4 g of sodium methoxide. Methyl iodide (20 g) was added and the reaction mixture was refluxed for 6 hours. The solvent was evaporated under reduced pressure and the residue treated with ether and water. The ether layer was separated and dried over magnesium sulphate. Evaporation of the solvent afforded α-methoxyimino-2-pyridine acetic acid methylester (Z and E-isomer respectively) as a colourless oil. The oxime compound was prepared by converting 2-pyridineacetic acid ethylester into the α-hydroxyimino derivative according to literature data (G. v. Zijl et al, J. Org. Chem. 26, 3375 (1961)). In contrast to the literature, a mixture of the E- and Z-isomers was obtained, which could be separated by fractional crystallization and/or column chromatography (silica gel with cyclohexane-ethyl acetate 1:1 as the eluant).

Z-isomer m.p. 102°–104° C. (methanol)
E-isomer m.p. 144°–146° C. (methanol).

EXAMPLE 12

Pyrazine carboxaldehyde, O-methyl oxime

In a similar manner to that described in Example 7, but starting form pyrazine carboxaldehyde (J. Org. Chem. 37, 111 (1972)), the title compound was obtained in a 60% yield m.p. 40°–41° C.

EXAMPLE 13

Pyrazine carboxaldehyde, O-methyl oxime

A solution of pyrazine carboxaldehyde diethyl acetal (3.6 g) and O-methylhydroxylamine hydrochloride (1.7 g) in 25 ml of alcohol was refluxed for 8 hours. The solvent was evaporated and the residue treated with chloroform and an aqueous solution of sodium bicarbonate. The chloroform layer was separated and dried over magnesium sulphate. Evaporation of the solvent and crystallization of the residual oil from petroleum ether (b.p. 40°–60° C.) afforded the title compound (1.3 g), m.p. 40°–41° C.

EXAMPLE 14 a. α-Methoxyimino-2-pyrazineacetonitrile-4-oxide (Z-isomer)

A mixture of Z-α-methoxyiminopyrazineacetonitrile (4 g), acetic acid (15 ml) and 30% hydrogen peroxide in water (15 ml) was heated at a temperature of 70° C. over one night. The reaction mixture was concentrated and treated with water and chloroform. The chloroform layer was separated and dried over magnesium sulphate. Evaporation of the solvent and successive crystallization of the residue from alcohol afforded Z-α-methoxyimino-2-pyrazineacetonitrile-4-oxide, m.p. 144°–145° C.

In a similar manner was prepared:

b. α-methoxyimino-2-pyridinylacetonitrile-1-oxide, m.p. 103°–105° C.

EXAMPLE 15

α-Methoxyimino-2-pyrazineacetonitrile-4-methiodide

A mixture of α-methoxyiminopyrazineacetonitrile Z-isomer (3.0 g) and methyl iodide (10 ml) was refluxed over one night. Excess methyl iodide was distilled off and the residue recrystallized from a mixture of methanol and toluene, affording the Z-isomer of α-methoxyimino-2-pyrazineacetonitrile-4-methiodide (4.7 g), m.p. 147°–148° C. (dec).

PHARMACOLOGICAL DATA

1. Anti-ulcer Activity

This was assessed by the inhibition of indomethacin-induced gastric damage in the rat according to the method of Elegbe (Israeli J. Med. Sci. (1974), 10, 1451).

Rats were starved overnight, given indomethacin subcutaneously (15 mg/kg) and sacrificed 5 hours later. Stomachs were inflated with 0.9% saline, cut along the greater curvature, pinned out and scored for gastric damage by the following system:

Score 1–3 according to the degree of erythema and slight haemorrhage.
Score 4–6 according to degree of mucosal erosion.
Score 7–9 according to depth of gastric damage.

Groups of 7 rats were used for each treatment level of compound, and a similar group receiving vehicle only was set up on each occasion of testing. Compound or vehicle was administered orally 30 minutes prior to, and at 2 hours post, dosing with indomethacin. Mean values per treatment were obtained using the above scoring system and the Mann Witney test applied for significance between such values. The mean inhibition of gastric damage from a number of experiments is shown in the following Table 1; the dosage being 100 mg/kg orally.

2. Effects on Gastric Secretion, in the Pyloric Ligated Rat

The method described by Shay, et al. (Gastroenterol (1945) 26, 906) was used. After overnight starvation the pylorus of a rat was ligated under halothane anaesthesia, the Compound vehicle only administered intraduodenally and the rats allowed to recover. They were sacrificed 3 hours later and the gastric juice removed. After measurement of the volume of secretion, its hydrogen ion concentration, [H+], was determined by titration with 0.05 N NaOH to pH 7. Groups of 4–6 animals were used for each treatment and the inhibitory effect of the Compound was ascertained by comparison of the mean values obtained with those from a simultaneously set up control group of animals which received vehicle only. Students 't' test was applied for significance between groups. The mean values for % inhibition obtained for a number of experiments are shown in the following Table 2, the dosage being 100 mg/kg i.d.

| Compound No.* | Table 1 % Inhibition | Table 2 % Inhibition Volume | Table 2 % Inhibition [H+] |
|---|---|---|---|
| 5 (Z-isomer) | 94 | 70 | 73 |
| 5 (E-isomer) | 96 | | |
| 6 a | 62 | 62 | |
| 6 b | 68 | 66 | 60 |
| 6 c | 43 | 52 | |
| 6 d | 50 | | |
| 6 e | | 62 | 48 |
| 6 f | | 46 | 20 |
| 6 g | 97 | 59 | |
| 6 h | 93 | 88 | |
| 6 i | 91 | 39 | 19 |
| 6 j | 73 | 43 | 22 |
| 6 k | | 80 | 24 |
| 6 l | 56 | 42 | 38 |
| 6 o | 48 | 74 | 41 |
| 6 q | 50 | | |
| 6 r | 61 | 46 | |
| 6 w | 83 | 90 | 56 |
| 6 x | 96 | 46 | 38 |
| 6 aa | | 35 | 23 |
| 6 bb | 72 | | |
| 6 cc | 95 | 80 | 39 |
| 6 dd | 77 | 35 | 39 |
| 6 ee | 84 | 28 | |
| 6 ff | 42 | | |
| 6 gg | 42 | | |
| 6 ll | 85 | 85 | 23 |
| 6 mm | 42 | 28 | |
| 6 nn | 79 | 28 | |
| 6 qq | 100 | 77 | 29 |
| 7 | | 74 | 33 |
| 8 (and 10) | 74 | 32+ | 24+ |
| 9 b | 56 | 26 | |
| 9 c | 65 | 40 | |
| 12 (and 13) | 66 | 42 | |
| 14 a | 91 | 50 | 34 |
| 15 | 55 | | |

+50 mg/kg
*The compound number is idential with the number of the Example wherein the preparation of the said compound is described.

3. Toxicity

No adverse effects were seen with single doses of compound no. 5 (Z-isomer) up to 536 or 824 mg/kg in mice and rats respectively. The acute oral median lethal dose of compound no. 5 is 1268 mg/kg in male mice and 2311 mg/kg in male rats.

What we claim is:

1. A pyrazinyl compound of the formula:

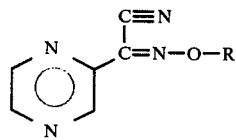

or a pharmaceutically acceptable salt thereof, wherein R is alkyl of 1 to 6 carbon atoms, cyanomethyl, alkenyl of 3 to 6 carbon atoms, alkynyl of 3 or 4 carbon atoms, cycloalkyl of 5 or 6 carbon atoms, or phenylalkyl of 1 to 3 carbon atoms in the alkyl group, said phenyl alkyl being unsubstituted or substituted in the phenyl ring with methoxy, chloro, nitro or cyano.

2. The compound according to claim 1 which is α-methoxyiminopyrazineacetonitrile.

3. The compound according to claim 1 which is α-ethoxyiminopyrazineacetonitrile.

4. The compound according to claim 1 which is α-allyloxyiminopyrazineacetonitrile.

5. The compound according to claim 1 which is α-propargyloxyiminopyrazineacetonitrile.

6. the compound according to claim 1 which is α-benzyloxyiminopyrazineacetonitrile.

7. The compound according to claim 1 which is cyanomethyloxyiminopyrazineacetonitrile.

8. A compound according to claim 1 which is substantially entirely in the form of the E or the Z isomer.

* * * * *

UNITED STATES PATENT AND TRADEMARK OFFICE
CERTIFICATE OF CORRECTION

PATENT NO. : 4,327,213
DATED : April 27, 1982
INVENTOR(S) : Jacob Adriaan Van Zorge It is certified that error appears in the above-identified patent and that said Letters Patent are hereby corrected as shown below:

On the Title Page, the correct name of the Assignee is ACF Chemiefarma NV.

Signed and Sealed this

Twenty-first Day of September 1982

[SEAL]

Attest:

GERALD J. MOSSINGHOFF

Attesting Officer

Commissioner of Patents and Trademarks